(12) United States Patent
Kuehne

(10) Patent No.: US 11,166,842 B2
(45) Date of Patent: Nov. 9, 2021

(54) METHOD AND APPARATUS FOR UNIFORM TOTAL BODY CRYOTHERAPY

(71) Applicant: Jonas Kuehne, Los Angeles, CA (US)

(72) Inventor: Jonas Kuehne, Los Angeles, CA (US)

(*) Notice: Subject to any disclaimer, the term of this patent is extended or adjusted under 35 U.S.C. 154(b) by 690 days.

(21) Appl. No.: 14/501,842

(22) Filed: Sep. 30, 2014

(65) Prior Publication Data

US 2016/0089262 A1 Mar. 31, 2016

(51) Int. Cl.
*A61F 7/00* (2006.01)
*F25D 3/10* (2006.01)
*F25D 17/06* (2006.01)

(52) U.S. Cl.
CPC .......... *A61F 7/0053* (2013.01); *F25D 17/067* (2013.01); *A61F 2007/0056* (2013.01); *A61F 2007/0062* (2013.01); *A61F 2007/0064* (2013.01); *F25D 3/102* (2013.01); *F25D 2317/063* (2013.01)

(58) Field of Classification Search
None
See application file for complete search history.

(56) References Cited

U.S. PATENT DOCUMENTS

| | | | |
|---|---|---|---|
| 5,660,046 A * | 8/1997 | de Langavant | F25D 3/105 62/239 |
| 6,698,210 B2 * | 3/2004 | Ogura | F25B 9/14 62/457.9 |
| 2010/0313579 A1 * | 12/2010 | Decourcelle | B60P 3/14 62/51.1 |
| 2012/0096873 A1 * | 4/2012 | Webber | F25D 19/006 62/48.1 |
| 2013/0068106 A1 * | 3/2013 | Hartmann | B01D 46/10 96/418 |
| 2015/0094702 A1 * | 4/2015 | Shuppo | A61F 7/0053 606/22 |

* cited by examiner

*Primary Examiner* — Jennifer Pitrak McDonald
*Assistant Examiner* — Elizabeth K So
(74) *Attorney, Agent, or Firm* — Omni Legal Group; Omid E. Khalifeh

(57) ABSTRACT

In accordance with one embodiment, a uniform total body cryotherapy method and apparatus operative to allow an individual in a cryotherapy chamber to be subjected to the same cold temperatures on their entire body at the same time. In use, the apparatus allows active dissemination of cold air in a confined space without the undesired consequence of wind shear commonly caused by forced movement of cold air.

6 Claims, 4 Drawing Sheets

METHOD AND APPARATUS FOR UNIFORM TOTAL BODY CRYOTHERAPY

CROSS-REFERENCE TO RELATED APPLICATIONS

None.

NOTICE OF COPYRIGHT AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by any one of the patent disclosure as it appears in the Patent and Trademark Office patent files or records, but otherwise reserves all copyright and trade dress rights whatsoever.

TECHNICAL FIELD

The present disclosure relates generally to methods and apparatuses for exposing a person's body to cold temperatures as a means of alleviating pain, decreasing inflammation, or achieving a general sense of well-being. More particularly, the present disclosure relates to a method and apparatus for facilitating the application of cryotherapy precisely and uniformly throughout the entire body of a person undergoing treatment.

DISCUSSION OF THE RELATED ART

The topical application of low temperatures have long been recognized as a form of medical therapy to relieve a variety of ailments ranging from inflammation to muscles spasms and even headaches. This technique, commonly referred to as cryotherapy, dates back to the sixteen hundreds in it's most primitive form when ice packs were used as a means of reducing inflammation through the constriction of blood vessels.

Various devices for utilizing cryotherapy throughout the body have been proposed. Many of these devices, such as those disclosed in U.S. Pat. Nos. 4,753,240, and 4,676,247, are limited to application on one region of the body at a time with particular attention on the hands an feet. Advances in the art have inspired more complex proposals for effectuating a desired treatment method through decreasing tissue temperature on and around the impacted area. U.S. Pat. No. 5,148,804 teaches an adjustable wrap structure capable of wrapping at least partially around various joints or body parts. While the '804 patent expands beyond just the hands and feet of the user, it lacks the ability to accurately and efficiently apply cryotherapy to more than one region of the body at a time.

The aforementioned techniques place significant constraints on how cold and for how long a practitioner could apply cryotherapy on their patient. Though these approaches were beneficial for the time, design constrictions only allowed small regions to be targeted and for a short period of time. Technological restrictions of the period meant temperatures could only be as cold as ice and not sustained for very long due to melting.

More recently, proposal have been made to address disadvantages of the the earliest disclosures. U.S. Pat. No. 8,162,930 overcomes the anatomical constraints using a method and device for cryogenic therapy applied on the whole body of a patient. In this disclosure, cryotherapy is performed by introducing the patient into a treatment cabin and exposing the body to cold air deposited into the cabin space. A vaporized solution comprising liquefied nitrogen is introduced into a chamber using piping and nozzles.

The manner in which cooling air is introduced into the chambers necessarily causes frigid air to accumulate in the bottom of the cryochamber. Over a short period, the air warms and expands rising towards the top of the chamber. The cold frigid air remains close to the bottom of the chamber causing a temperature gradient. Accordingly, an individual standing in the proposed chamber will be exposed to warmer temperatures on their upper extremities and substantially colder temperatures at and around their lower extremities. In practice, clinicians are limited in the amount of time they can allow patients to spend in these chambers and must focus on the exposure time of the lower extremities alone or risk harming their patients. Skin burns to the lower extremities are a well known risk associated with these devices. Accordingly patients must be removed from the chambers before the upper extremities are able to receive the full benefits of treatment.

All of the cyrochambers heretofore known are further limited because they are incapable of treating the entire body of the person within. These devices only go about as far as the upper shoulder of the person inside. As a result, they do not supply cooling air to the head and neck of the user. The head and neck comprise many cold receptors and ignoring this region has a deleterious impact on the treatments efficacy.

Proposals have also been made to use fans as a means of forcing the cold air up towards the higher extremities. However, attempts at this methods have proven ineffective. The movement of cold air results in wind shear. This wind shear factor unnecessarily exposes the patient to a high risk of skin burn causing medical professionals to dismiss this as a viable treatment option.

Finally, U.S. Pat. No. 8,316,652 teaches a mobile cryotherapy system without overcoming the health hazards introduced by the '930 patent. Furthermore, neither the '652 patent nor the '930 patent teaches an adequate means for ensuring the cold air introduced into the chambers does not escape. Temperatures within the chambers may range from minus eighty to minus one hundred and sixty degrees Celsius and yet all of the cryotherapy chambers heretofore known utilize conventional insulation methods which have proven inadequate for sustaining these temperatures.

Accordingly, there exists a need for a cryotherapy apparatus and method that can deliver cold air uniformly to all the extremities of a patient undergoing treatment. There further exists a need for such an apparatus which may accomplish these objectives in an efficient manner without substantial waste resulting from inadequate isolation. The present invention facilitates these and other needs currently experienced by professionals practicing in the field of cryotherapy.

SUMMARY

A method and apparatus are provided for the uniform application of cooled air simultaneously to the upper and lower body of an individual undergoing cryotherapy. The present disclosure overcomes the challenges presented by the prior art through the use of a cooling and distribution apparatus capable of creating and maintaining a temperature within a cryochamber ranging between −80 and −160 degrees Celsius. The apparatus of the present disclosure facilitates the cryotherapy treatment process by creating an environment comprising no significant temperature variation between the space occupied by the patients upper and lower extremities.

Briefly described, one embodiment, among others, is a uniform total body cryotherapy apparatus operative to allow an individual in a cryotherapy chamber to be subjected to the same cold temperatures on their upper and lower extremities at the same time. In use, the apparatus allows active dissemination of cold air in a confined space without the undesired consequence of wind shear commonly caused by forced movement of cold air.

The apparatus of the present disclosure comprises a heat exchanger, circulating means, ductwork, cryogenic material, or cooling agent, and a means for containing the same, a deflecting means, and an air-permeable shield. The refrigeration means of the present disclosure varies in composition and function from any other heretofore taught by the prior art. A cooling agent travels from the containment unit through a plurality of heat exchangers to an outlet where it can be discarded. Positioned behind the heat exchangers is a length of ductwork comprising an entry opening and exit opening through which air may travel.

The refrigeration means further comprise a circulating apparatus such as a motorized fan operative to direct airflow through the ductwork entry and out the exit near which a deflecting means is positioned. The deflecting means comprises an input side and an output side. The deflecting means is operative to redirect air originating from the circulating apparatus to the space directly in front of the heat exchangers. Accordingly, the deflecting means must be sufficiently wide so that the output side extends beyond the plurality of heat exchangers of the refrigeration means.

In one embodiment, cold air is blown downward through the ductwork from a circulating apparatus positioned above the entry side and deflected back up and past the cooling fins of the heat exchangers. Unlike the prior art references, where the person inside the chamber is sprayed with cooling agent onto their skin, at no point does the apparatus of the present disclosure expose any person inside directly to the cooling agent. The temperature of the air is reduced as it follows a path towards the cryochamber ceiling. This will cause the cooled air to slowly sink down towards the bottom of the chamber. The result is an even distribution of cold air from floor to ceiling without any wind shear effect on the person inside the chamber.

Another embodiment may further comprise a permeable membrane positioned between the heat exchangers and space occupied by a user. Such a membrane will be operative to shield the user from touching the heat exchangers while still allowing passive insertion of cold air through the membrane. By way of example, and not limitation, such a membrane may be comprised of wood or plastic.

In one embodiment of the present disclosure, the cooling agent may be recycled as part of a closed loop. In this embodiment, the cooling agent is passed through an initial set heat exchangers but not discarded through a vent pipe. Rather than being discarded, the used cooling agent passes through a line connected to a separate set of heat exchangers where it facilitates the cooling of another cryochamber. The second cryochamber is not as cool as the original chamber. This establishes a gradient of chambers whereby the user may begin by entering a chamber with the highest temperature and gradually work their way into successively colder chambers.

The chambers may be interconnected while maintaining their respective temperatures using adequately sealed access doors as a means for physical separation. In certain embodiments of the present disclosure, each individual chamber may comprise it's own refrigeration means comprising individualized heat exchangers, circulating means, ductwork, a deflecting means, and an air-permeable shield. Each refrigeration means may be supplied by solution from the same cryogenic material tank or comprise an independent tank to supply it.

By way of example, one such cryogenic material solution may be comprised of liquid nitrogen. The amount of cooling agent entering the heat exchangers may be regulated in a number of different ways. In one embodiment, this is accomplished using at least one valve on a line which connects the agent storage chamber to the heat exchangers. In one embodiment, this valve may be electronically coupled to a temperature sensor monitoring the inside of any give chamber.

Having a primary chamber separated from other ancillary chambers functions to minimize temperature loss from the chamber with the lowest temperature. Temperature loss within a cyrochamber can lead to wasteful energy expenditures. Numerous other features, objects and advantages of the invention will become apparent from the following description when read in conjunction with the accompanying drawings.

DESCRIPTION OF THE DRAWINGS

Figures

Figure 1:
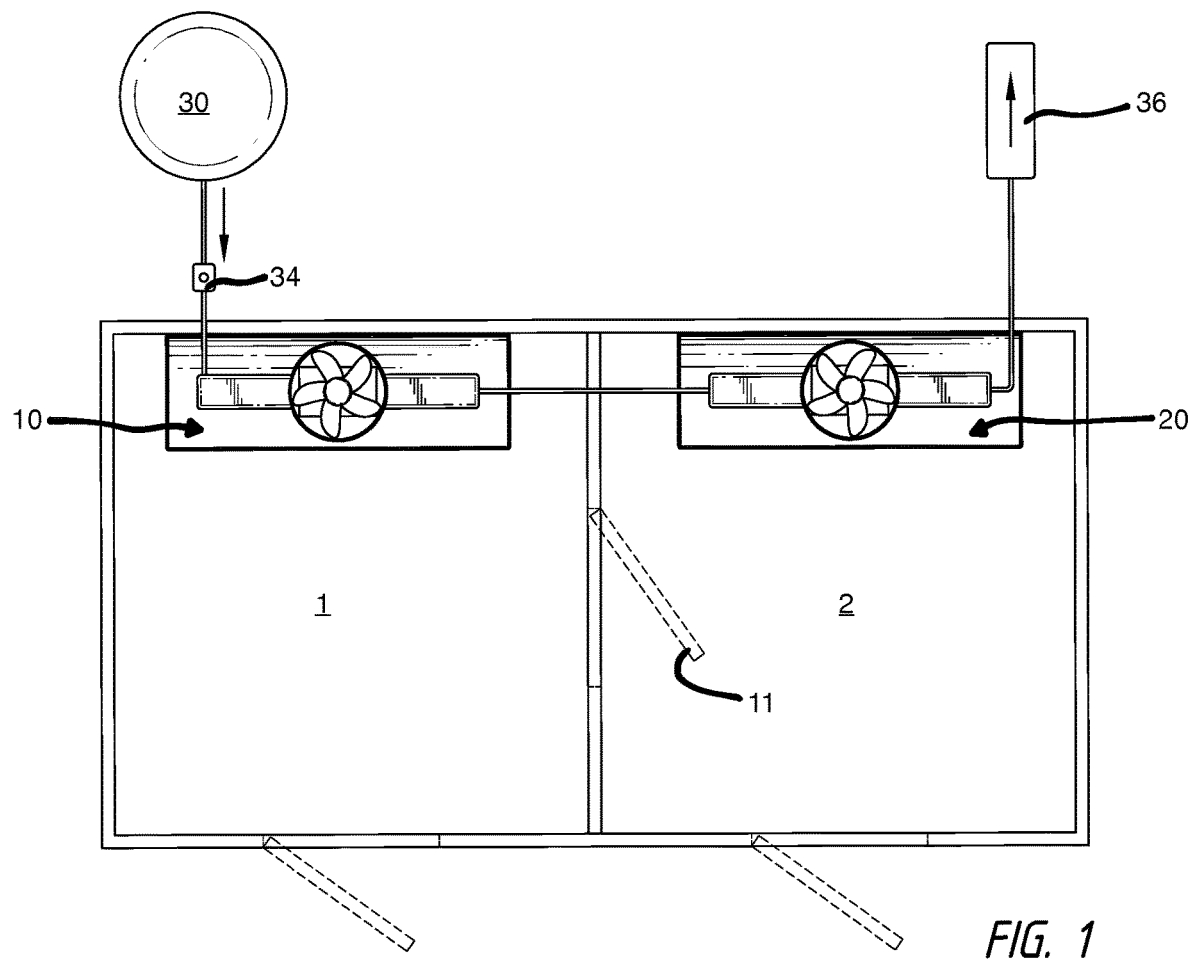
FIG. 1 is an overhead schematic depicting a first exemplary cryochamber of the present disclosure.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein.

The terms "couple," "coupled," "couples," "coupling," and the like should be broadly understood and refer to connecting two or more elements or signals, electrically, mechanically or otherwise. Two or more electrical elements may be electrically coupled, but not mechanically or otherwise coupled; two or more mechanical elements may be mechanically coupled, but not electrically or otherwise coupled; two or more electrical elements may be mechanically coupled, but not electrically or otherwise coupled. Coupling (whether mechanical, electrical, or otherwise) may be for any length of time, e.g., permanent or semi-permanent or only for an instant.

DETAILED DESCRIPTION

Illustrative embodiments of the invention are described below. The showings are for purposes of illustrating preferred embodiments and not for purposes of limiting the same. The following explanation provides specific details for a thorough understanding of an enabling description for these embodiments. One skilled in the art will understand that the invention may be practiced without such details.

FIG. 1 is an overhead schematic depicting an first exemplary cryochamber utilizing the method and apparatus of the present disclosure. The exemplary embodiment illustrated therein depicts a cryochamber comprising at least two subchambers. A primary chamber 1 and a secondary chamber 2 are interconnected and separated by an access door 11 which remains closed during normal operation. This embodiment further comprises at least two cooling apparatuses, a first apparatus 10 located in the primary chamber 1 and a second apparatus 20 located in the secondary chamber 2. However, in various embodiments, only one cooling apparatus will be used within a single chamber. In addition, this embodiment comprises at least one containment unit 30 for storing a cooling agent (not shown), at least one control valve 32, and an outlet 36 for discarding used cooling agent through a discharge conduit.

Figure 2:
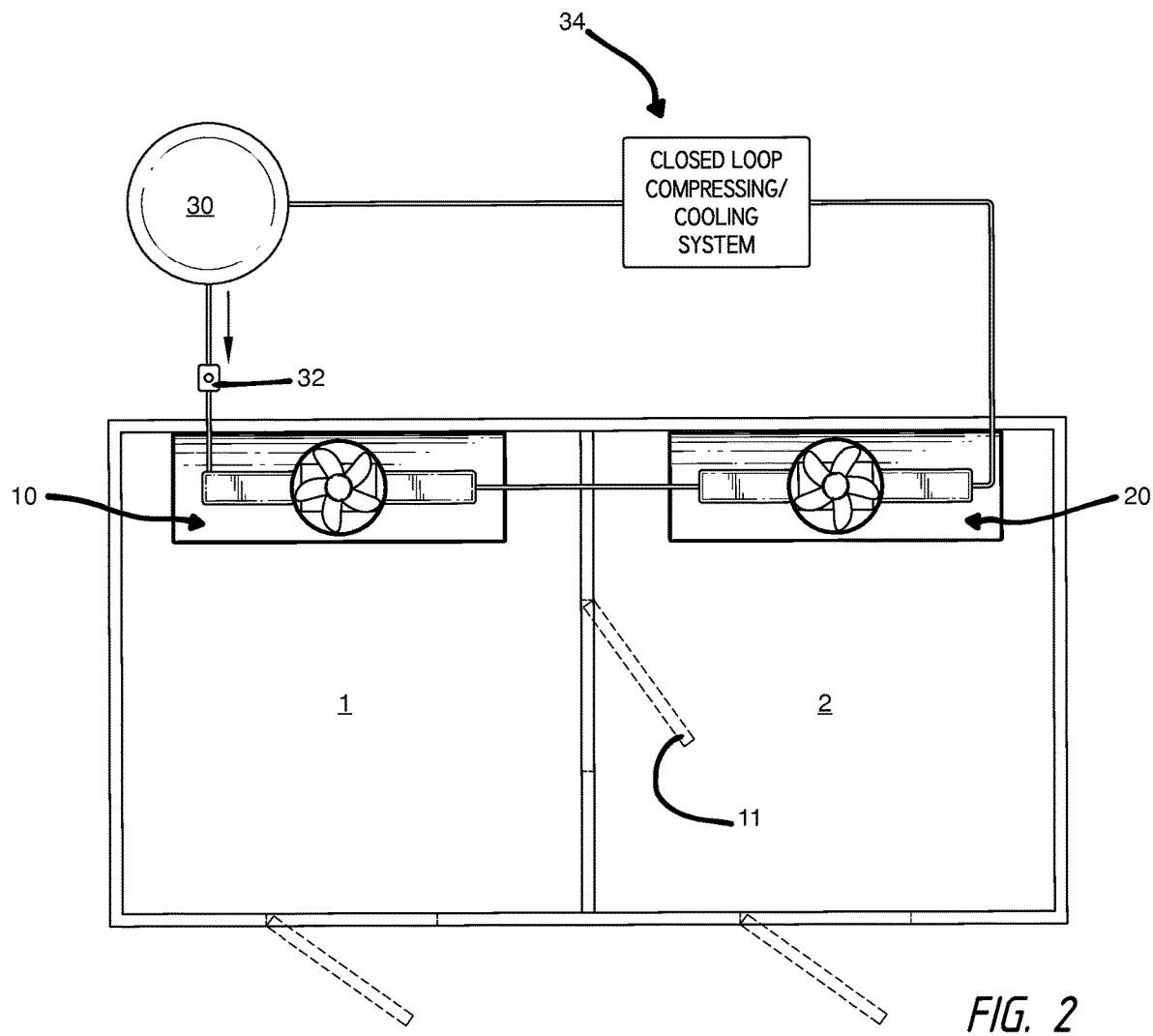
FIG. 2 is an overhead schematic depicting a second exemplary cryochamber of the present disclosure.

In another embodiment, depicted in FIG. 2, the outlet 36 is removed and a cooling agent compressing and cooling means 34 is added. It is further envisioned that, in some embodiments of the present disclosure, both a cooling means 34 and outlet 36 will be included as parts of the apparatus 10.

Opening the control valve 32 in FIG. 1, causes cooling agent to be dispensed from the containment unit 30 to the first cooling apparatus 10. After the agent passes through this cooling apparatus 10, the temperature in the primary chamber 1 is cooled but the cooling agent need not be discarded. Conversely, the cooling agent may pass from the first cooling apparatus 10 to the second cooling apparatus 20. In this embodiment, the cooling agent passes through the second apparatus 20 while cooling the atmosphere in the secondary chamber 2 to a slightly lesser degree than the primary chamber 1. Finally, it exits the secondary chamber 2 to were it may be discarded through an outlet 36.

FIG. 2 is an overhead schematic depicting a second exemplary cryochamber utilizing the method and apparatus of the present disclosure in a closed-looped configuration. The exemplary embodiment illustrated herein depicts a cryochamber comprising at least two subchambers. A primary chamber 1 and a secondary chamber 2 are interconnected and separated by an access door 11 which remains closed during normal operation. This embodiment also comprises at least two cooling apparatuses, a first apparatus 10 located in the primary chamber 1 and a second apparatus 20 located in the secondary chamber 2. In addition, this embodiment comprises at least one containment unit 30 for storing a cooling agent (not shown), at least one control valve 32, and a cooling agent compressing and cooling means 34.

Similar to the example in FIG. 1, opening the control valve 32 in FIG. 2, causes cooling agent to be dispensed from the containment unit 30 to the first cooling apparatus 10. After the agent passes through this cooling apparatus 10, the temperature in the primary chamber 1 is cooled but the cooling agent need not be discarded. Conversely, the cooling agent may pass from the first cooling apparatus 10 to the second cooling apparatus 20. In this embodiment, the cooling agent passes through the second apparatus 20 while cooling the atmosphere in the secondary chamber 2 to a slightly lesser degree than the primary chamber 1. However, in this embodiment instead of being discarded through an outlet 36, the cooling agent is channeled through to a compression and cooling means 34. When the agent is directed to the compression and cooling means 34, it regains most of its original composition before moving back into the containment unit 30 to be reused.

In one embodiment of the present disclosure, the cryochamber may further comprise a system controller (not shown) which may be programmed to regulate the temperatures within each chamber. The system controller may receive information from a plurality of sensors located within the chambers which may include, but are not limited to, temperature sensors, thermostats, cooling agent control means, control valves, and the like. The system controller communicates with the control valves and the cooling apparatuses to properly maintain the temperatures within a desired range. This is accomplished by regulating the flow of cooling agent as well as the operation of the cooling apparatuses. In one embodiment, it is envisioned the temperatures within the cyrochambers may be further regulated by opening and closing vents to the environment outside any given chamber.

Preferably, the cryochamber walls and access doors are thermally insulated to minimize temperature loss from within each respective chamber.

Figure 3:
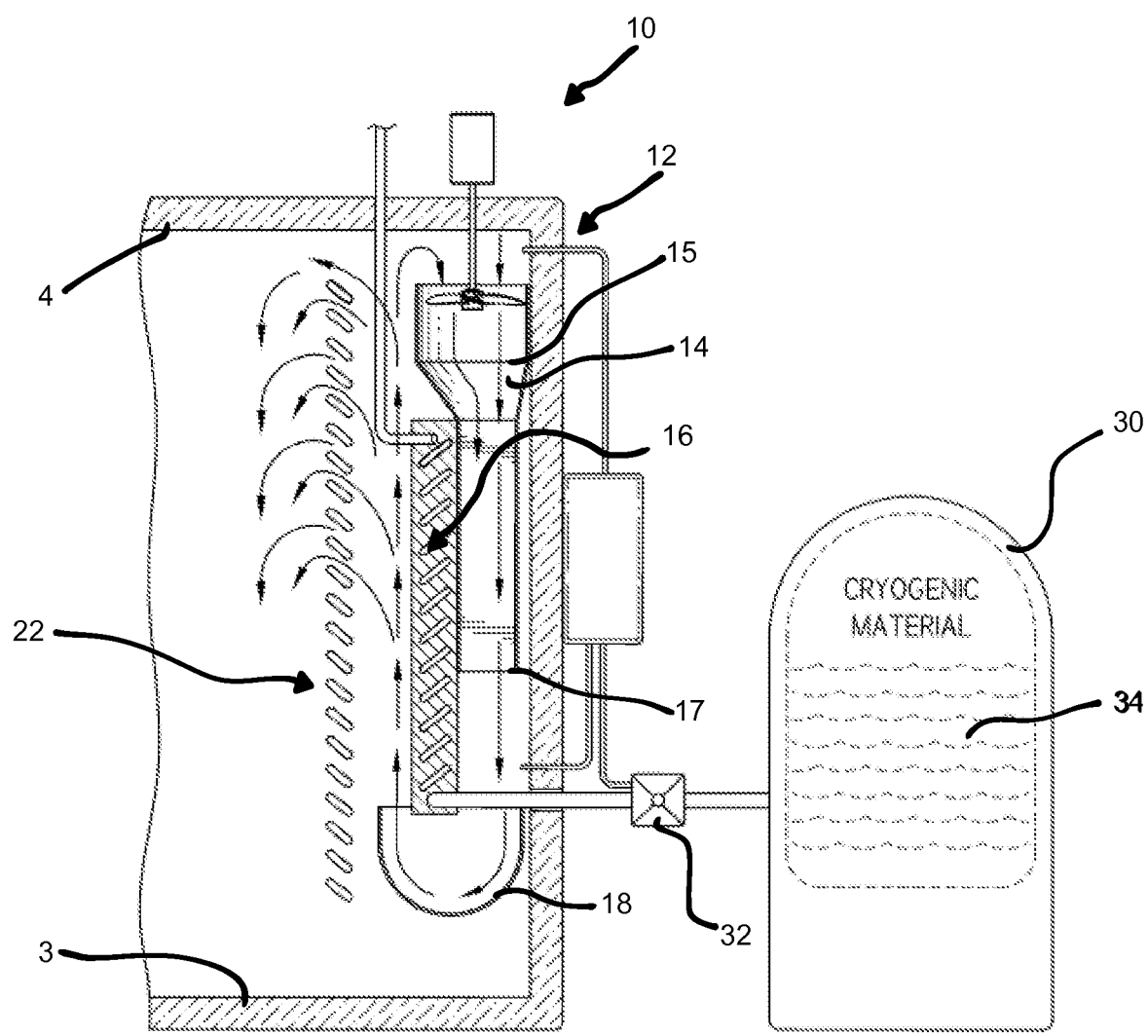
FIG. 3 is a profile view illustrating the inner workings of an exemplary cryochamber.

FIG. 3 is a profile view illustrating the inner workings of the cooling apparatus. In this instance, the first cooling apparatus 10 is shown along with ductwork connecting it to the cooling agent 31 containment unit 30. This figure further illustrates the air flow through the cooling apparatus 10 which allows the cyrochamber to maintain substantially uniform temperatures from floor 3 to ceiling 4. The apparatus 10 depicted in FIG. 2 comprises an air circulation means 12, such as a motorized fan, ductwork 14 positioned behind a plurality of heat exchangers 16, a deflecting means 18, as well as a permeable membrane 22 that also functions to shield the occupants of the cryochamber from contact with the heat exchangers.

In FIG. 3, the circulation means 12 is operative to channel air through the ductwork 14 which comprises an entry 15 and an outlet 17. The airflow in FIG. 3 travels downward from the entry 15 through the ductwork 14 and past the outlet 17 to the deflecting means 18. The deflecting means 18 is illustrated as a U-shaped pan by way of example, and not limitation. The deflecting means 18 is wide enough to capture the airflow traveling through the ductwork 14 and protrudes beyond the width of the heat exchangers 16. This ensures air traveling behind the heat exchangers 16 is redirected upward to the area in front, after being redirected by the deflecting means 18.

FIG. 3 illustrates the flow of circulating air once it has been deflected towards the side of the heat exchangers 16 opposite the ductwork 14. This air contacts a plurality of cooling fins located on the heat exchangers 16 as it travels back up towards the ceiling 4. The blown air moving passed these fins gets colder while on this trajectory and gradually sinks back down towards the chamber floor 3. As a result, the air on the chamber floor 3 has the same temperature as the any air making it all the way up to the ceiling 4. Furthermore, this objective has been accomplished without any undesired generation of wind shear on the person inside the chamber.

The system controller may be set to maintain the cryochamber temperature within a predetermined set point, e.g. minus one hundred and forty degrees Celsius or a range, e.g., minus eighty degrees Celsius and minus one hundred and eighty degrees Celsius. If one of the sensors detects a temperature rise above the set point, the system controller responds by sending a signal operative to open a valve 32 permitting cooling agent to flow from the containment unit 30 therethrough and into the heat exchangers 16. This happens until the sensed temperature drops back down below the set point. The system controller responds accordingly by closing the valve 32 and terminating the flow of cooling agent until the cryochamber temperature rises above the set point temperature Should the heat exchangers 16 contact a users skin while in operation, the results could be harmful. The permeable shield 22 depicted in FIG. 2 is operative to shield users from the heat exchangers 16 while continuing to allow passive insertion of cooled air through pours, slits, or channels contained therein. Such a membrane may be comprised of a variety of different materials including, but not limited to, wood and plastic.

In one embodiment, air traveling upwards after passing the front of the heat exchangers 16 will be recirculated back down through the ductwork 14 by the circulation means 12.

In yet another embodiment, the ductwork 14 entry point 15 may be wider than the outlet 17. Such a design will facilitate acceleration of blown air by the circulating means 12. Accordingly, air moving out of the duct 14 will be traveling at a higher rate of speed than the air coming in. This encourages deflection while ensuring more blown air is directed back up past the heat exchangers 16 towards the ceiling 4.

Figure 4:
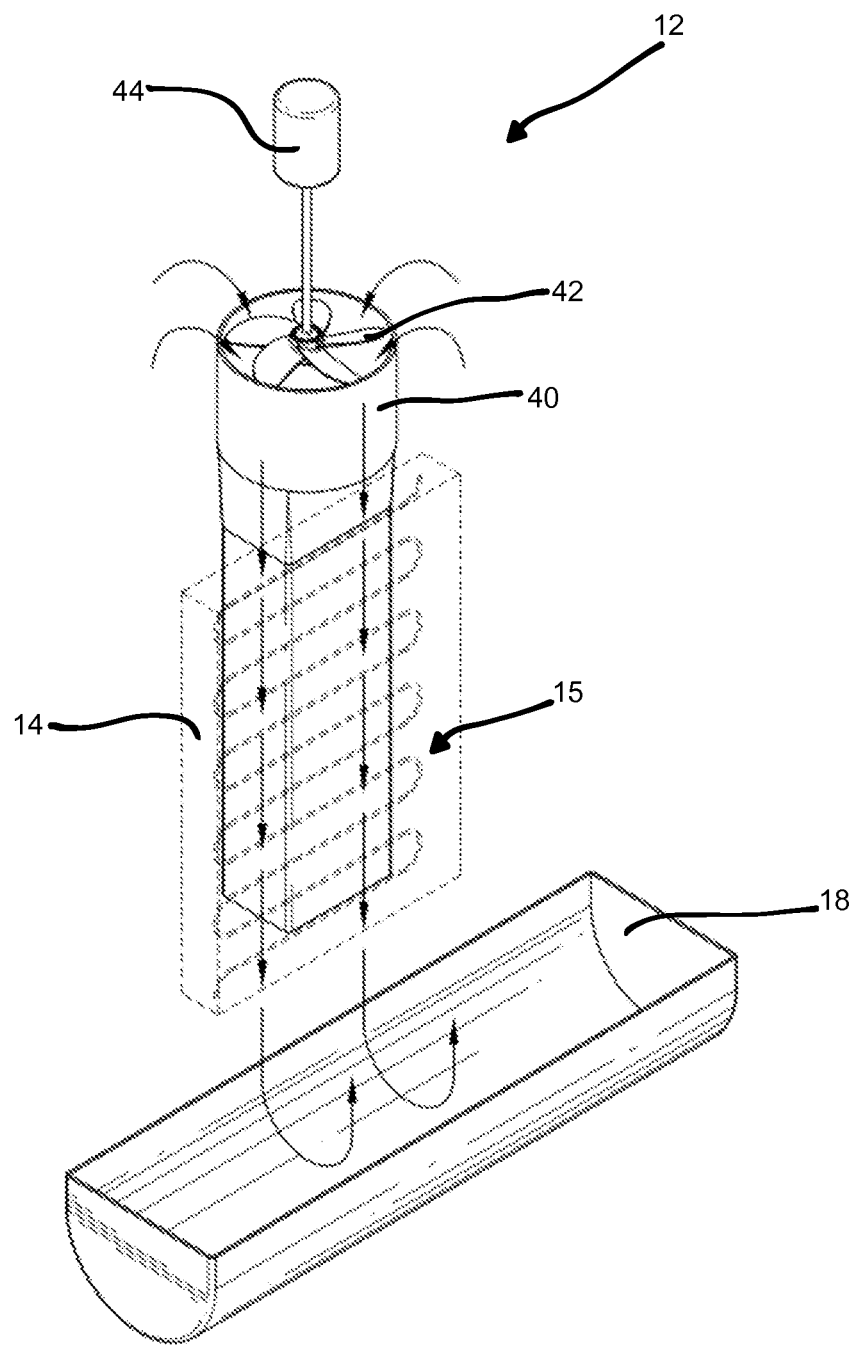
FIG. 4 is a perspective view of a cooling apparatus of the present disclosure.

FIG. 4 further illustrates the various components of the cooling apparatus 12. The downward trajectory of air blown by the circulation means 12 is facilitated by a ring member 40 surrounding a plurality of blades 42. The blades 42, are driven by a motor 44 and may be angled to direct air flow towards the deflection means 18. In one embodiment, the distance between the distal end of the blades 42 and the inner wall of the ring member 40 will be small. Minimizing this distance enhances the apparatuses air channeling capabilities ensuring optimal movement of air to the ductwork 14 below. In one embodiment, this capability is further enhanced by positioning the blades 42 within the ring member 40 rather than protruding from it.

Although the invention has been described with reference to specific embodiments, it will be understood by those skilled in the art that various changes may be made without departing from the scope of the invention. Accordingly, the disclosure of embodiments is intended to be illustrative of the scope of the invention and is not intended to be limiting. It is intended that the scope of the invention shall be limited only to the extent required by the appended claims. To one of ordinary skill in the art, it will be readily apparent that the devices and method discussed herein may be implemented in a variety of embodiments, and that the foregoing discussion of certain of these embodiments does not necessarily represent a complete description of all possible embodiments. Rather, the detailed description of the drawings, and the drawings themselves, disclose at least one preferred embodiment, and may disclose alternative embodiments.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents

CONCLUSIONS, RAMIFICATIONS, AND SCOPE

While a particular form of the invention has been illustrated and described, it will be apparent that various modifications can be made without departing from the spirit and scope of the invention. For example, the cryotherapy chamber is illustrated as being comprised of two distinct cooling apparatuses in two distinct cryochambers in some embodiments even though the inventors contemplate the possibility that it may comprise only one cooling apparatus in only one cyrochamber or more cryochambers and event the possibility for each cryochamber having more than one cooling apparatus. Accordingly, it is not intended that the invention be limited, except as by the appended claims.

The teachings provided herein can be applied to other systems, not necessarily the method and apparatus described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Particular terminology used when describing certain features or aspects of the invention should not be taken to imply that the terminology is being refined herein to be restricted to any specific characteristics, features, or aspects of the method and apparatus for uniform total body cryotherapy with which that terminology is associated. In general, the terms used in the following claims should not be constructed to limit the method and apparatus to the specific embodiments disclosed in the specification, unless the above description section explicitly define such terms. Accordingly, the actual scope encompasses not only the disclosed embodiments, but also all equivalent ways of practicing or implementing the disclosed method and apparatus. The above description of embodiments of the method and apparatus is not intended to be exhaustive or limited to the precise form disclosed above or to a particular field of usage. While specific embodiments of, and examples for, the method and apparatus for uniform total body cryotherapy are described above for illustrative purposes, various equivalent modifications are possible which those skilled in the relevant art will recognize.

While certain aspects of the method and apparatus for uniform total body cryotherapy are presented below in particular claim forms, the inventors contemplate the various aspects of the method and apparatus in any number of claim forms. Accordingly, the inventors reserve the right to add additional claims after filing the application to pursue such additional claim forms for other aspects of the method and apparatus for uniform total body cryotherapy.

What is claimed is:

1. An apparatus for uniform total body cryotherapy without exposing a user to cryogenic material, comprising:
    at least one open loop cryochamber, said cryochamber comprising a floor, a ceiling, a space between said floor and said ceiling with sufficient dimensions to contain at least one living person undergoing cryotherapy, air within the cryochamber; and
    a first cooling apparatus capable of utilizing a cryogenic material so as to maintain the temperature of said cryochamber at any particular set point between −80° C. and −160° C. from said floor to said ceiling and having at least one heat exchanger configured to contain cryogenic material;
    an air circulating means positioned proximate to the ceiling of the cryochamber and operative to blow air downward behind the at least one heat exchanger; and
    a deflection means positioned proximate to the floor of the cryochamber and operative to redirect air blown downward behind the at least one heat exchanger to a space in front of the at least one heat exchanger;
    wherein the cryotherapy is a procedure to treat physical ailments.

2. The apparatus of claim 1 further comprising a duct positioned behind the at least one heat exchanger, wherein the air circulating means is positioned above said duct.

3. The apparatus of claim 1 further comprising a shielding means positioned in front of the at least one heat exchanger wherein said shielding means is a permeable membrane operative to allow passive airflow therethrough.

4. The apparatus of claim 1 further comprising a second cryochamber wherein said second cryochamber comprises a floor, a ceiling, a space between said floor and said ceiling with sufficient dimensions to contain at least one living person undergoing cryotherapy, air within the second cryochamber, a second cooling apparatus coupled to said first cooling apparatus; wherein said cryogenic material may pass from said first cooling apparatus to said second cooling apparatus, thereby cooling the air within the second cryochamber to a lesser degree than the first cryochamber.

5. The apparatus of claim 4 further comprising an outlet through which used cryogenic material is expelled.

6. The apparatus of claim 4 further comprising a compression and cooling means and a containment unit wherein cryogenic material originating from said second cooling apparatus passes through said compression and cooling means into said containment unit.

* * * * *